(12) United States Patent
Bierman et al.

(10) Patent No.: US 6,413,240 B1
(45) Date of Patent: Jul. 2, 2002

(54) DIALYSIS CATHETER ANCHORING SYSTEM

(75) Inventors: Steven F. Bierman, Del Mar; Richard A. Pluth, San Diego; Wayne T. Mitchell, Cardiff, all of CA (US)

(73) Assignee: Venetec International, Inc., San Diego, CA (US)

( * ) Notice: Subject to any disclaimer, the term of this patent is extended or adjusted under 35 U.S.C. 154(b) by 33 days.

(21) Appl. No.: 09/630,582

(22) Filed: Aug. 3, 2000

(51) Int. Cl.⁷ .............................................. A61M 5/32
(52) U.S. Cl. ................. 604/174; 604/180; 128/DIG. 26
(58) Field of Search .................. 604/174, 180, 604/179; 128/DIG. 26; 292/304, 341.1

(56) References Cited

U.S. PATENT DOCUMENTS

| | | |
|---|---|---|
| 2,525,398 A | 10/1950 | Collins |
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raffaelli, Sr. |
| 3,630,195 A | 12/1971 | Santomieri |
| 3,677,250 A | 7/1972 | Thomas |
| 3,766,915 A | 10/1973 | Rychlik |
| 3,856,020 A | 12/1974 | Kovac |
| 3,896,527 A | 7/1975 | Miller et al. |
| 3,906,946 A | 9/1975 | Nordström |
| 3,973,565 A | 8/1976 | Steer |
| 4,020,835 A | 5/1977 | Nordstrom et al. |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,161,177 A | 7/1979 | Fuchs |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,326,519 A | 4/1982 | D'Alo et al. |
| 4,362,156 A | 12/1982 | Feller, Jr. et al. |
| 4,392,853 A | 7/1983 | Muto |

(List continued on next page.)

FOREIGN PATENT DOCUMENTS

| | | |
|---|---|---|
| EP | 0064284 A2 | 10/1982 |
| EP | 356683 A | 3/1990 |
| FR | 2381529 | 9/1978 |
| GB | 2288542 A | 10/1995 |
| WO | WO 92/19309 | 11/1992 |

*Primary Examiner*—Denise L. Esquivel
*Assistant Examiner*—Marc Norman
(74) *Attorney, Agent, or Firm*—Knobbe, Martens, Olson & Bear, LLP

(57) ABSTRACT

An anchoring system for securing a dialysis catheter to a patient comprises an anchor pad and a retainer. The anchor pad is attached to the skin of the patient by an adhesive layer on one side of the pad. The retainer is disposed upon the surface of the anchor pad opposite the adhesive layer and includes a base and a cover and a adhesive spot. A groove upon the base is arranged to receive a Y-site portion of a dialysis catheter where the lumens merge distal to the insertion site. A post also protrudes from the base to the cover at a position which will be disposed between the two distal branches of the dialysis catheter. The cover closes over the base, securing the Y-site between the groove and the post. Closing the cover also places at least a portion of the catheter in contact with the adhesive spot. This contact between the retainer, adhesive spot and catheter thereby inhibits inadvertent motion of the catheter upon the patient. A latch mechanism is disposed upon the retainer to maintain the cover in a closed position over the Y-site of the catheter on the base.

9 Claims, 10 Drawing Sheets

U.S. PATENT DOCUMENTS

| | | |
|---|---|---|
| 4,397,647 A | 8/1983 | Gordon |
| 4,405,163 A | 9/1983 | Voges et al. |
| 4,449,975 A | 5/1984 | Perry |
| 4,453,933 A | 6/1984 | Speaker |
| 4,480,639 A | 11/1984 | Peterson et al. |
| 4,711,636 A | 12/1987 | Bierman |
| 4,742,824 A | 5/1988 | Payton et al. |
| 4,808,162 A | 2/1989 | Oliver |
| 4,852,844 A | 8/1989 | Villaveces |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,955,864 A | 9/1990 | Hajduch |
| 4,976,700 A | 12/1990 | Tollini |
| 4,997,421 A | 3/1991 | Palsrok et al. |
| 5,037,397 A | 8/1991 | Kalt et al. |
| 5,073,170 A | 12/1991 | Schneider |
| 5,084,026 A | 1/1992 | Shapiro |
| 5,098,399 A | 3/1992 | Tollini |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| 5,195,981 A | 3/1993 | Johnson |
| 5,248,306 A * | 9/1993 | Bierman ..................... 604/283 |
| 5,266,401 A | 11/1993 | Tollini |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman et al. |
| 5,338,308 A | 8/1994 | Wilk |
| 5,342,317 A | 8/1994 | Claywell |
| 5,344,406 A | 9/1994 | Spooner |
| 5,354,282 A | 10/1994 | Bierman |
| 5,368,575 A | 11/1994 | Chang |
| 5,380,293 A | 1/1995 | Grant |
| 5,382,239 A | 1/1995 | Orr et al. |
| 5,389,082 A | 2/1995 | Baugues et al. |
| 5,398,679 A | 3/1995 | Freed |
| 5,403,285 A | 4/1995 | Roberts |
| 5,413,562 A | 5/1995 | Swauger |
| 5,443,460 A | 8/1995 | Miklusek |
| 5,456,671 A | 10/1995 | Bierman |
| 5,468,231 A | 11/1995 | Newman et al. |
| 5,470,321 A | 11/1995 | Forster et al. |
| D364,922 S | 12/1995 | Bierman |
| B15,147,322 A | 1/1996 | Bowen et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,527,293 A | 6/1996 | Zamierowski |
| D375,355 S | 11/1996 | Bierman |
| 5,578,013 A | 11/1996 | Bierman |
| 5,643,217 A | 7/1997 | Dobkin |
| 5,685,859 A | 11/1997 | Kornerup |
| 5,693,032 A | 12/1997 | Bierman |
| 5,702,371 A | 12/1997 | Bierman |
| D389,911 S | 1/1998 | Bierman |
| 5,722,959 A | 3/1998 | Bierman |
| 5,800,402 A | 9/1998 | Bierman |
| 5,810,781 A * | 9/1998 | Bierman ..................... 604/174 |
| 5,827,239 A | 10/1998 | Dillion et al. |
| 5,833,667 A * | 11/1998 | Bierman ..................... 604/180 |
| 6,132,398 A * | 10/2000 | Bierman ..................... 604/174 |
| 6,213,979 B1 * | 4/2001 | Bierman ..................... 604/174 |
| 6,224,571 B1 * | 5/2001 | Bierman ..................... 604/174 |
| 6,231,548 B1 * | 5/2001 | Bassett ..................... 604/174 |
| 6,283,945 B1 * | 9/2001 | Bierman ..................... 604/174 |
| 6,290,676 B1 * | 9/2001 | Bierman ..................... 604/174 |

* cited by examiner

DIALYSIS CATHETER ANCHORING SYSTEM

BACKGROUND OF THE INVENTION

1. Field of the Invention

This invention relates to an anchoring system for securing a medical article to a patient. More specifically, this invention relates to an anchoring system which retains a dialysis catheter in position upon a patient without crimping and which may be used with catheters that remain in position for extended periods.

2. Description of the Related Art

It is common in kidney dialysis procedures to use a catheter inserted into a major vein near the heart to facilitate the blood exchange necessary for dialysis. Because dialysis procedures must generally be performed on a regular basis, it is not uncommon for such a catheter to be left in place in between dialysis sessions. This may reduce the potential risks to the patient associated with having to reintroduce such a catheter prior to each session.

Other risks, however, arise when leaving such a catheter in position for extended periods of time. It can be very dangerous for the patient if the catheter moves substantially in either axial direction. Inadvertent withdrawal of the catheter may lead to bleeding, either internally or externally, and axial advancement of the catheter may press the catheter tip into the heart or other sensitive internal tissue.

Furthermore, leaving such a catheter in position on the patient traditionally requires a taped dressing near the insertion site. The use of such adhesives at the insertion site may retain dirt or other contaminant particles, potentially leading to infection of the patient. Additionally, removal of taped dressings may itself cause undesired motion of the catheter upon the patient.

An additional drawback to using taped dressings near the insertion site is that they require periodic changes. The frequent, often daily, removal and reapplication of adhesive tape to the skin of the patient can excoriate the skin in the area around the dressing. This is especially problematic for dialysis patients, as their skin tends to be more fragile and sensitive to abrasion due to collagen deficiency common to renal conditions. Such repeated applications of tape over the catheter may also lead to the build up of adhesive residue on the outer surface of the catheter. This residue can result in contaminants adhering to the catheter itself, increasing the likelihood of infection of the insertion site. This residue may also make the catheter stickier and more difficult to handle for medical attendants.

For these reasons, a need exists for an improved dialysis catheter retainer which may be used on patients where the catheter remains in place over an extended period of time.

SUMMARY OF THE INVENTION

In accordance with one aspect of the present invention, a retainer for releasably securing a portion of a medical article, such as a dialysis catheter, to a patient includes an adhesive spot located upon the inner surface of a channel of the retainer. The retainer has a cover and a base which are coupled by a flexible hinge, such that the cover may be opened. The channel is formed by a groove disposed on the base of the retainer and a corresponding groove disposed on the cover of the retainer. When the cover is closed over the base of the retainer, the two grooves form a channel through the retainer. The adhesive spot desirably has a tacky surface which frictionally inhibits any lateral or longitudinal motion of the retained portion of the medical article through the channel of the retainer. Furthermore, the transverse thickness of the adhesive spot is such that the adhesive spot presses against the retained portion of the medical article when the cover is in the closed position and the medical article passes through the channel of the retainer, thereby inhibiting transverse motion of the retained portion of the medical article.

In accordance with another aspect of the present invention, a retainer for releasably securing a portion of a medical article is constructed with a compressible member within the channel of the retainer. This allows the retainer to accommodate medical articles with different transverse heights within the same retainer. When a retainer of thicker transverse dimension than that of the channel opening is closed within the retainer, the medical article will be pressed into the compressible member, squeezing it transversely. This compression of the member will result in a more secure fit between the channel of the retainer and the medical article.

In accordance with a further aspect of the present invention, a retaining member is provided within the channel of a retainer for releasably securing a portion of a branched medical article. The retaining member is disposed within this channel such that when the cover of the retainer is in the closed position, the retaining member separates one end of the channel into two separate passages. In this way, branching medical articles, such as dialysis catheters, can be inhibited from longitudinal movement because the retaining member lies between the two distal branches of the medical article.

In accordance with an additional aspect of the present invention, a latching mechanism for use with a retainer comprises a keeper disposed upon the cover and a latch disposed upon the base of the retainer. The keeper comprises at least one member capable of interengaging with at least a portion of the latch on the base, and the latch comprises at least a recess which accepts at least a portion of the member of the keeper when the cover is in the closed position. The keeper further comprises an operator lever which may be actuated by the fingertip of a medical attendant by pressing downwardly upon it to deflect the bar of the keeper inward, disengaging the member from the recess of the latch.

It is understood that the retainer can take various modes, and not all modes need include all of the aspects noted above. Thus, for example, those skilled in the art will recognize that the invention may be embodied or carried out in a manner that utilizes one of or a group of the noted aspects and features of the invention, without necessarily using all such aspects and features.

In a preferred mode of the present invention, a retainer for securing a medical article to a patient comprises a base and cover which form a channel, as described above, and a compressible adhesive spot is disposed on the surface of this channel. In this way, the retainer inhibits motion of the retained portion of the medical article in the longitudinal, lateral, and transverse directions and also allows the retainer to accommodate medical articles of varying transverse heights. A latching mechanism is disposed in part on the base and in part on the cover of the retainer so as to selectively secure the retainer in the closed position.

In another preferred mode of the present invention, an anchoring system for a medical article is created using a retainer as described above with an anchor pad. The anchor pad provides an adhesive lower surface for attaching to the skin of a patient, and the upper surface is attached to the retainer. The retainer preferably has a substantially disc shaped base which provides a stable surface with which to attach the retainer to the upper surface of the anchor pad. This arrangement allows the medical article to be anchored to the skin of the patient, and also allows the selective release of the medical article from the retainer so as to facilitate changing the anchoring system without removing the medical article from the patient.

In a further preferred mode of the present invention, a catheterization system comprises a catheter including a branching site and an anchoring system as described for securing this catheter to a patient. The catheter is one which includes a single elongated body extending proximally from one side of the branching site and at least two elongated bodies extending distally from the other side of the branching site, thereby forming a "Y" shaped junction, or "Y-site."

In another preferred mode of the present invention, the catheter includes a winged portion which is disposed proximally of the Y-site of the catheter. This winged portion is wider than the width of the channel of the retainer. By placing the winged portion immediately proximal of the retainer, the winged portion will be inhibited from migrating distally into the channel by its width, providing additional securement to the catheter.

In an additional preferred aspect of the present invention, the medical article is secured axially with respect to the patient by use of a device as described above. The medical article is placed within the groove of the base of the retainer, and then the cover is closed over the medical article. In this way the medical article is held within the retainer of the anchoring system. The anchoring system may then be adhered to the skin of the patient at a suitable location, thereby inhibiting any motion between the patient and the medical article.

Further aspects, features and advantages of this invention will become apparent from the detailed description of the preferred embodiment which follows.

BRIEF DESCRIPTION OF THE DRAWINGS

The above mentioned and other features of the invention will now be described with reference to the drawings of a preferred embodiment of the present anchoring system. The illustrated embodiment of the anchoring system is intended to illustrate, but not to limit the invention. The drawings contain the following figures.

DETAILED DESCRIPTION OF THE PREFERRED EMBODIMENT

The following description and examples illustrate a preferred embodiment of the present anchoring system in detail which is disclosed in the context of use with an exemplary dialysis catheter. The principles of the present invention, however, are not limited to dialysis catheters. It will be understood by those of skill in the art in view of the present disclosure that the anchoring system described can be used with other types of medical articles, including, but not limited to: other catheters, fluid delivery tubes, and electrical wires. One skilled in the art may also find additional applications for the devices and systems disclosed herein. Thus, the illustration and description of the anchoring system in connection with a dialysis catheter is merely exemplary of one possible application of the anchoring system.

Figure 1:
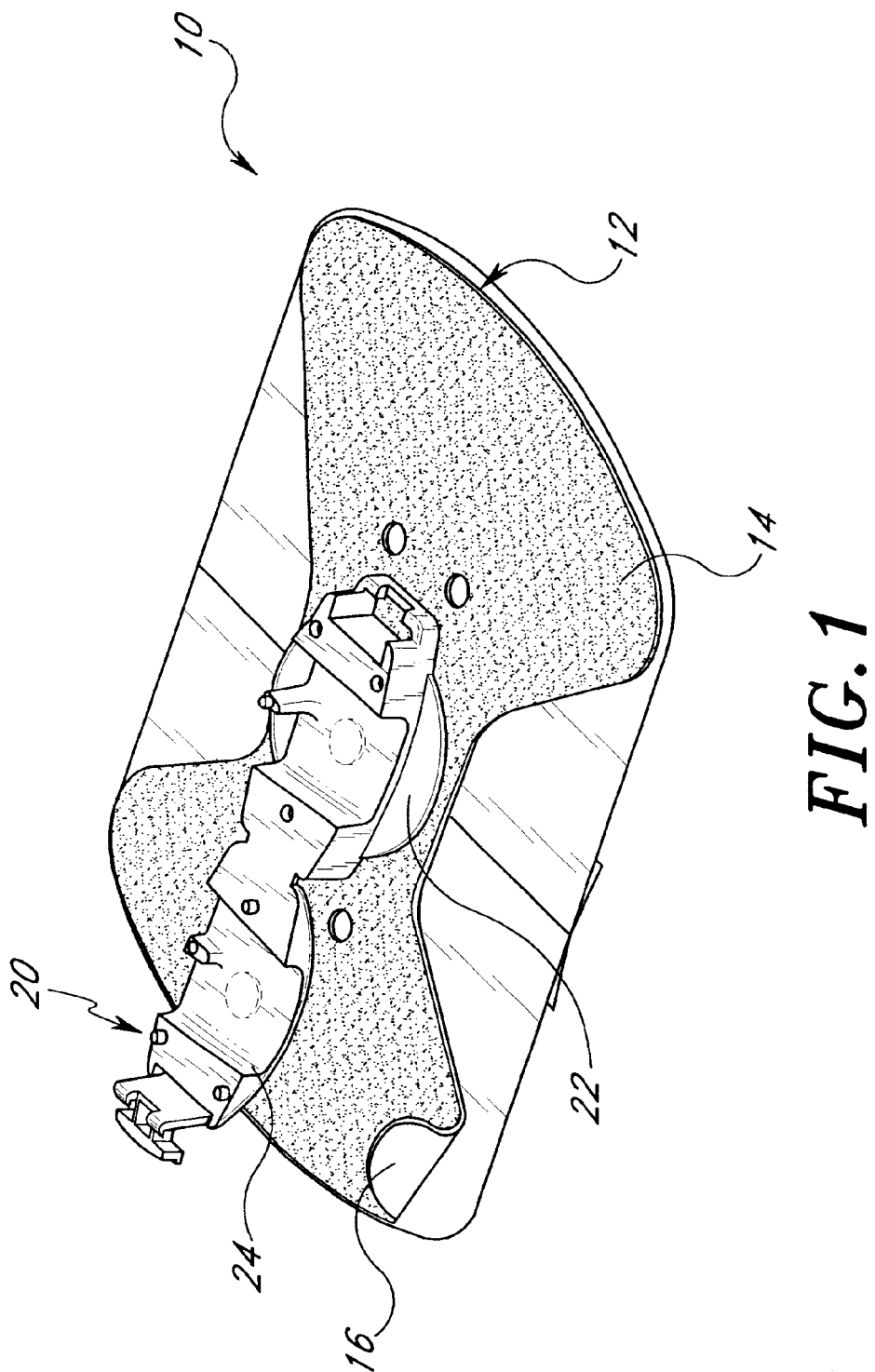
FIG. 1 illustrates an anchoring system in accordance with a preferred embodiment of the present invention in perspective view with the cover open.

To assist in the description of these components of the anchoring system (see FIG. 1), the following coordinate terms are used. A "longitudinal axis" is generally parallel to the section of the catheter retained by the anchoring system 10. A "lateral axis" is normal to the longitudinal axis and is generally parallel to the plane of an anchor pad 12, as seen in FIG. 1. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the catheter, and therefore is substantially synonymous with the term "longitudinal" as used herein. Also, the terms "proximal" and "distal", which are used to describe the present anchoring system, are used consistently with the description of the exemplary applications. Thus, proximal and distal are used in reference to the center of the patient's body. The terms "upper," "lower," "top," "bottom," and the like, which also are used to describe the present anchoring system, are used in reference to the illustrated orientation of the embodiment. A detailed description of a preferred embodiment of the anchoring system, and its associated method of use, now follows.

Overview

As shown in FIG. 1, the described embodiment comprises an anchoring system 10 in two main components: the anchor pad 12 and a retainer 20. As noted above, the anchoring system can form a component of a catheterization system that also includes one or more medical articles (e.g., a dialysis catheter).

The retainer 20 is mounted upon the anchor pad 12 and the anchor pad is secured to the skin of the patient, generally by an adhesive disposed upon the bottom surface of the pad. The retainer receives the medical article and secures it in position. The retainer itself comprises several sub-components, including a base, a cover, at least one adhesive spot, and one or more retaining members. The releasable engagement of the medical article is achieved, at least in part, by cooperation between the adhesive spot, the base and the cover. Because the cover may be opened after the medical article is secured, it is possible for the medical article to be removed from the anchoring system for any necessary purpose, such as to replace the anchoring system or to facilitate moving the patient. This removal of the medical article from the anchoring system can be accomplished without removing the anchoring system from the patient if desired.

The medical article is held in position through a combination of lateral and transverse pressure along the secured portion of the medical article within a channel of the retainer. In the illustrated embodiment, the channel is formed between grooves disposed upon the base and the cover of the retainer. Lateral pressure is provided between the walls of the grooves and the sides of the Y-site of the retained medical article, and transverse pressure is provided by the bottom and upper portions of the channel and the adhesive spot. When the cover is closed and secured into the closed position by the latching mechanism, these forces inhibit the tube from moving substantially in either the lateral or transverse directions. Longitudinal motion of the tube is inhibited by the friction of the adhesive spot against the catheter, as well as by the tapered shape of the channel itself.

Furthermore, the embodiment described provides a universal feature such that the anchoring system can be used to receive and secure a variety of sizes of medical articles. Because the securing forces are provided in part by a compressible adhesive spot, a variety of catheters of varying transverse heights may be accommodated. Furthermore, the frictional nature of the adhesive spot allows for the channel to provide additional shear forces to retain the catheter within the channel.

The anchoring system also desirably releasably engages the catheter. This allows the anchoring system to be disengaged from the catheter without removing the catheter for any of a variety of known purposes. For instance, the healthcare provider may wish to remove the anchoring system in order to change the anchor or clean the insertion site without removing the catheter from the patient. In situations where the catheter is in position in the patient for an extended period of time, it is advantageous to periodically change the anchor to maintain the best positional securement of the catheter. For these purposes, it is desirable that the disengagement of the catheter from the anchoring system can be accomplished without removing the catheter from the patient.

Before describing the present anchoring system in detail, a brief description of a dialysis catheter is provided to assist the reader's understanding of the exemplary embodiment that follows. As best understood from FIG. 14, the catheter 8 includes a proximal tip which will be inserted into a large vein in the chest cavity, such as the vena cava. The interior of the catheter has two independent lumens, each of which has an opening near the proximal tip. The catheter includes a Y-site 112 where the two lumens separate and above which each has a separate branch of the catheter. The lumens of these branches assume either a coaxial or side-by-side arrangement on the proximal side of the Y-site 112 to form a main catheter body 118. On the distal side of the Y-site 112, a webbing may extend between the two branches 114, 116 at a point next to the Y-site 112. The Y-site 112 may also include a generally triangular plastic housing within which the branching of the lumens takes place.

Figure 2:
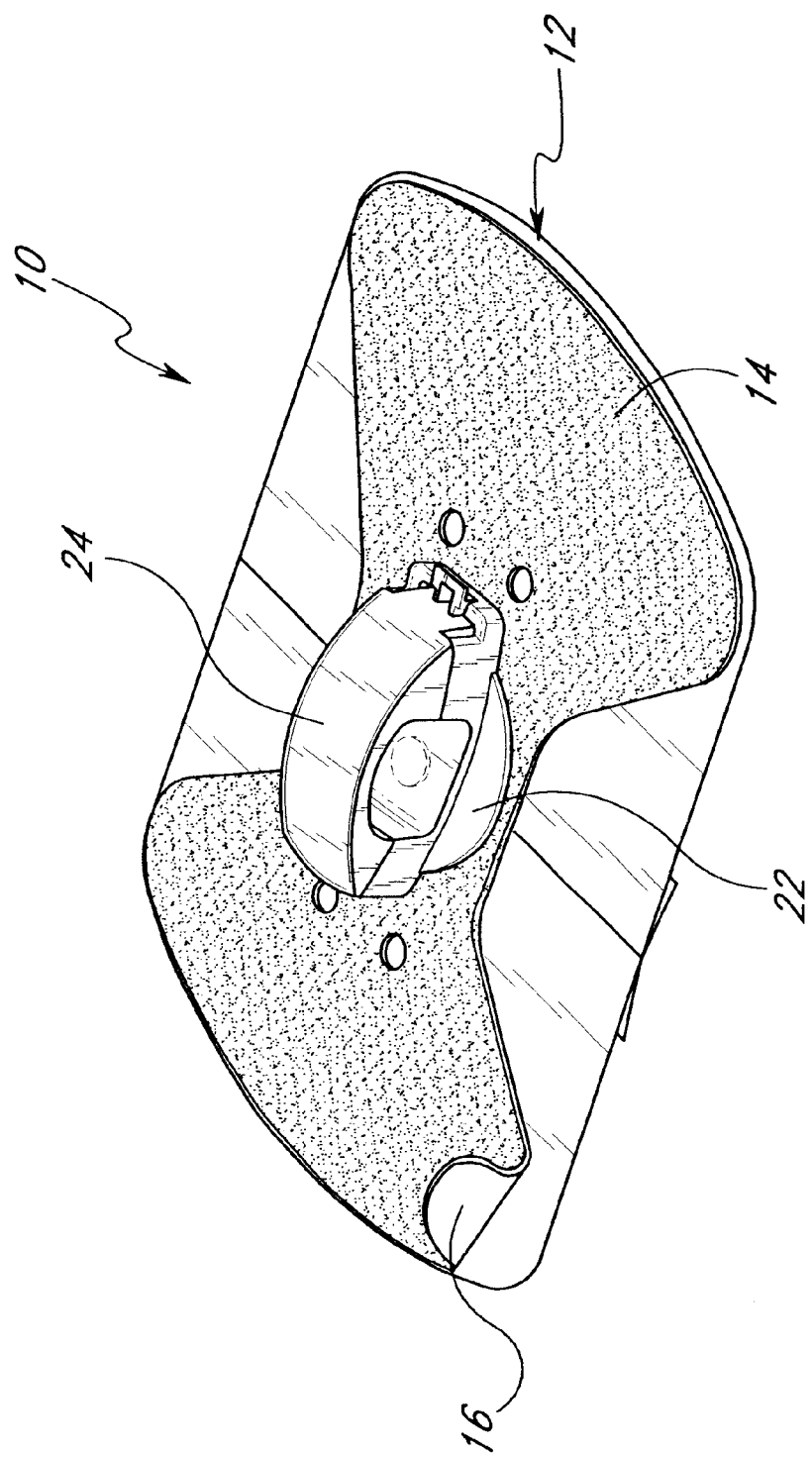
FIG. 2 illustrates a perspective view of the anchoring system of FIG. 1 with the cover closed.
Figure 3:
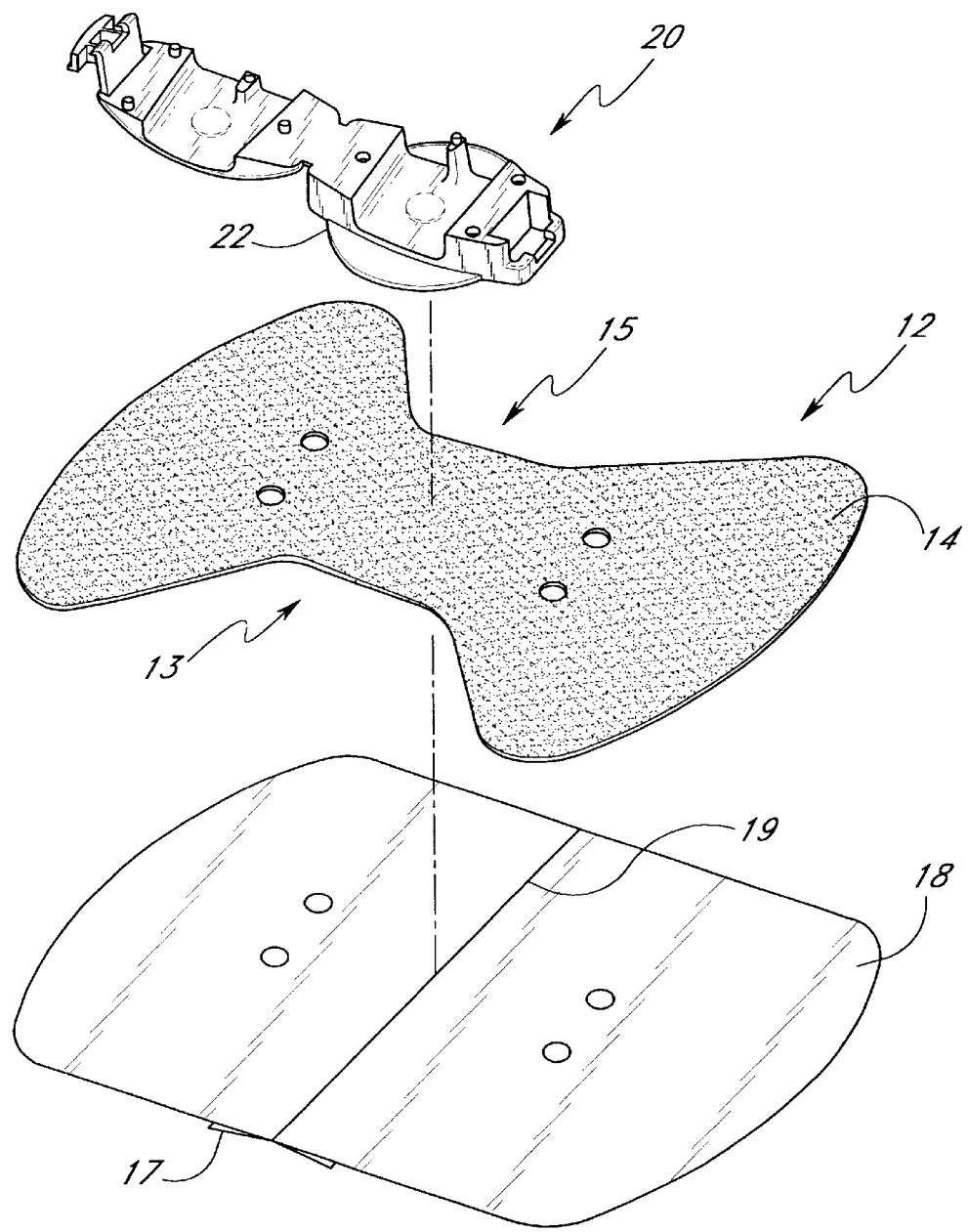
FIG. 3 illustrates an exploded perspective view of the anchoring system of FIG. 1.

With reference now to FIGS. 1 to 3, the anchoring system 10 includes an anchor pad 12 and a retainer 20. The anchor pad 12 secures the retainer 20 to a patient's skin. The anchor pad 12 has a lower adhesive surface 16 which adheres to the skin of a patient and a roughened upper surface 14 which supports a retainer 20. The retainer 20 is configured to accept and retain a section of a dialysis catheter within the anchoring system 10. In the illustrated embodiment, the retainer comprises a base 22 and a cover 24. The cover 24 is releasably secured to the base 22 and moveable between open and closed positions.

Anchor Pad

FIGS. 1 to 3 illustrate an anchor pad 12 which desirably comprises a laminate structure with an upper foam layer (e.g., closed-cell polyethylene foam), and a lower adhesive layer. The lower adhesive layer constitutes the lower surface 16 of the anchor pad 12. The lower surface 16 desirably is a medical-grade adhesive and can be either diaphoretic or nondiaphoretic, depending upon the particular application. Such foam with an adhesive layer is available commercially from Avery Dennison of Painsville, Ohio. Although not illustrated, it will be understood that the anchor pad 12 can include suture holes in addition to the adhesive layer to further secure the anchor pad 12 to the patient's skin.

In an alternative embodiment, a hydrocolloid adhesive may advantageously be used upon the anchor pad 12 for attaching the anchor pad to the skin of the patient. The hydrocolloid adhesive has less of a tendency to excoriate the skin of a patient when removed. This may be particularly important for patients whose skin is more sensitive or fragile, such as those with a collagen deficiency, common to dialysis patients.

As shown in FIG. 3, a surface of the upper foam layer constitutes an upper surface 14 of the anchor pad 12 (see FIG. 2). The upper surface 14 can be roughened by corona-treating the foam with a low electric charge. The roughened or porous upper surface 14 can improve the quality of the adhesive joint (which is described below) between the base 22 and the anchor pad 12. In the alternative, the flexible anchor pad 12 can comprise a medical-grade adhesive lower layer, an inner foam layer and an upper paper or other woven or nonwoven cloth layer.

A removable paper or plastic release liner 18 desirably covers the adhesive lower surface 16 before use. The liner 18 preferably resists tearing and desirably is divided into a plurality of pieces to ease attachment of the pad to a patient's skin. In the illustrated embodiment, the liner 18 is split along a center line 19 of the flexible anchor pad 12 in order to expose only half of the adhesive lower surface 16 at one time.

The liner 18 length, as measured in the lateral direction, extends beyond the center line 19 of the anchor pad 12 and is folded over, or back onto the liner 18. This folded over portion defines a pull tab 17 to facilitate removal of the liner 18 from the adhesive lower surface 16. A medical attendant uses the pull tab 17 by grasping and pulling on it so that the liner 18 is separated from the lower surface 16. The pull tab 17 overcomes any requirement that the medical attendant pick at a corner edge or other segment of the liner 18 in order to separate the liner 18 from the adhesive layer. The pull tab 17 of course can be designed in a variety of configurations.

For example, the pull tab 17 can need not be located along a center line 19 of the anchor pad 12; rather, the pull tab 17 can be located along any line of the anchor pad 12 in order to ease the application of the anchor pad 12 onto the patient's skin at a specific site. For example, an area of a patient's skin with an abrupt bend, such as at a joint, can require that the pull tab 17 be aligned toward one of the lateral ends of the anchor pad 12 rather than along the center line 19.

As best seen in FIG. 3, the anchor pad 12 also desirably includes a pair of opposing concave sections 13, 15 that narrows the center of the anchor pad 12 proximate to the base 22. As a result, the lateral sides of the anchor pad 12 have more contact area which provides greater stability and adhesion to a patient's skin.

Retainer

Figure 4:
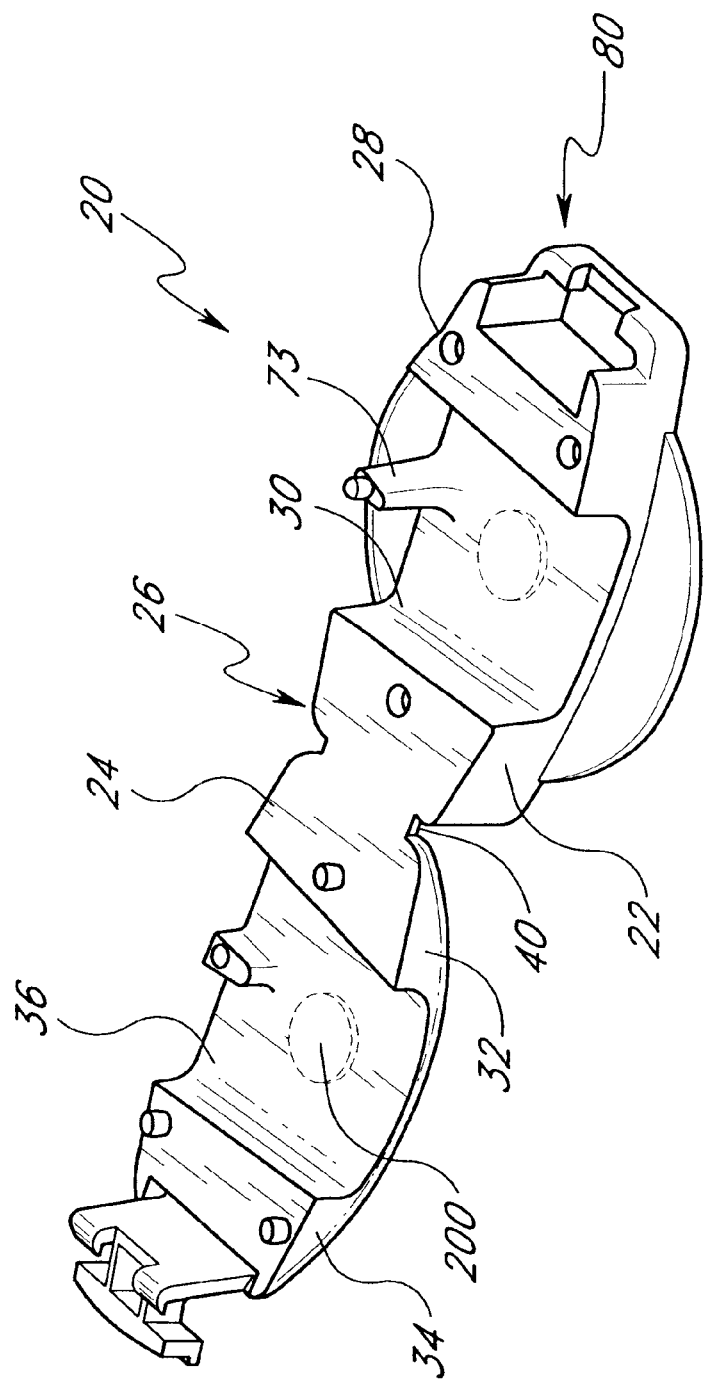
FIG. 4 illustrates an enlarged perspective view of the retainer of the anchoring system of FIG. 1.

With reference now to FIGS. 4 to 9, the retainer 20 includes a rigid structure principally formed by the base 22 and the cover 24 (see FIG. 4). In the illustrated embodiment, the base 22 and cover 24 are integrally formed to comprise a unitary retainer 20. This can be accomplished in any of a variety of ways well known to those skilled in the art. For instance, the entire retainer 20 can be injection molded in order to reduce fabrication costs.

Additionally, as will be apparent from the below description, several features of the retainer, such as the latch 80 and hinge 40, are desirably flexible. Suitable rigid but flexible materials include for example without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. The illustrated retainer 20 preferably is formed by injection molding using polyethylene or polypropylene material. However, other materials can be utilized, and the retainer 20 can comprise a non-unitary base 22 and cover 24.

With reference to FIG. 4, a base 22 in the illustrated embodiment comprises an elongated body of a generally parallelepiped shape. The base 22, however, can be configured in a wide variety of shapes as well, such as circular, square, triangular or the like in order to suit a particular application. Furthermore, the lower surface of the base is desirably substantially disc shaped. This provides a larger surface at the bottom of the retainer for use in attaching the lower surface of the base to the upper surface of the anchor pad. This disc shaped lower surface improves the attachment between the retainer and anchor pad, and also provides greater stability to the retainer upon the skin of the patient.

It is advantageous for the longitudinal dimension of the base 22 to be sufficiently long to provide stability to the catheter 8 along its length. In this way, the longitudinal length of the retained catheter portion is sufficient to inhibit rocking of the catheter 8 relative to the retainer 20 (i.e., to prevent the retainer 20 from acting as a fulcrum for the catheter). Also, the lateral dimension of the base 22 desirably allows the healthcare provider to easily and naturally grip the base 22, and also provides space on which to locate a hinge 40 and a portion of the latch mechanism 80.

As shown in FIG. 4, the base 22 includes first and second sides 26, 28. The first side 26 lies generally at one lateral end of the base 22, and the second side 28 lies at an opposite lateral end of the base 22.

Figure 5:
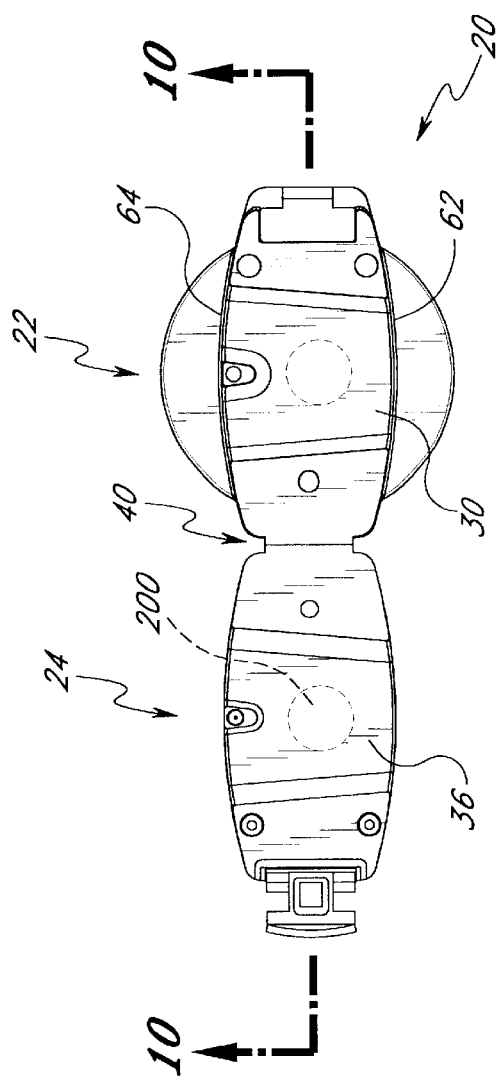
FIG. 5 illustrates a top plan view of the retainer of FIG. 4.

A groove 30 is formed on the baste 22 between the first side 26 and the second side 28. In the illustrated embodiment, the groove 30 has generally a curvilinear cross-sectional shape. As best seen in FIG. 5, the lower groove 30 is also varied in width (i.e., in the lateral direction) along its longitudinal length. That is, in the illustrated embodiment, the side walls of the lower groove 30 diverge from each other in a generally linear manner from one longitudinal side of the retainer 20 to the other longitudinal side of the retainer.

The base 22 of the retainer 20 is attached to the upper surface 14 of the anchor pad 12. The base 22 desirably is secured to the upper surface 14 by a solvent bond adhesive, such as cyanoacrylate or other bonding material. One such adhesive is available commercially as Part No. 4693 from the Minnesota Mining and Manufacturing Company (3M).

As also seen in FIG. 4, the cover 24 has an elongate shape which desirably is substantially coextensive with the planar size and shape of the base 22. However, the cover need not be precisely the same size or shape as the base 22. For instance, the cover 24 can be sized to extend beyond any of the lateral, traverse, or longitudinal edge of the base 22. The cover may also be sized so as to not extend to a particular lateral, traverse, or longitudinal edge of the base 22. The cover can also include a skirt or flange that extends over and/or about the base 22 or any portion thereof.

The cover 24 desirably has a sufficient size to cover the lower groove 30 in the base (see FIG. 8) and to accommodate a portion of the latch mechanism 80 and the hinge 40 which operate between the base 22 and the cover 24, as described below. The cover 24 also desirably is of a dimension which provides for easy manipulation. For example, the cover's size easily accommodates the grasp of a medical attendant.

The cover 24 includes a first side 32 which lies generally at one lateral end of the cover 24 as shown in FIG. 4. The first side 32 of the cover therefore generally corresponds to the first side 26 of the base 22. The cover 24 also has a second side 34. The second side 34 lies generally toward a lateral end of the cover 24, opposite of the first end, and corresponds generally to the second side 28 of the base 22.

Figure 6:
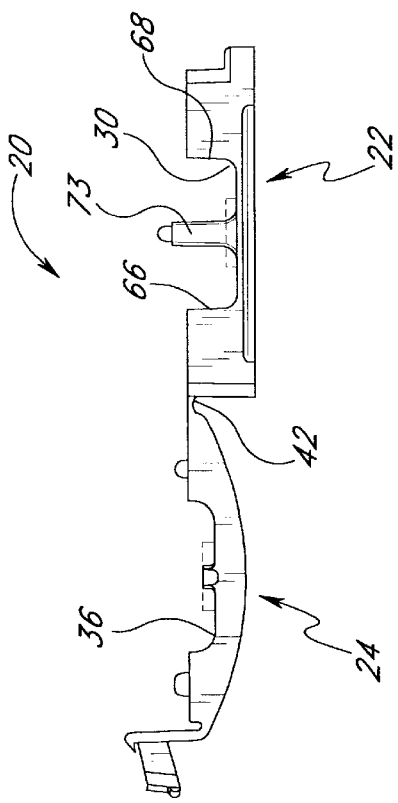
FIG. 6 illustrates a proximal side view of the retainer of FIG. 4.

An upper groove 36 is formed on an inner side of the cover 24 between the first and second sides 32, 34 of the cover 24 and corresponds generally to the lower groove 30 formed in the base 22 (see FIGS. 5 and 6). The width of the upper groove 36 is also varied in the lateral direction along its longitudinal length. That is, in the illustrated embodiment, the side walls of the upper groove 36 diverge from each other in a generally linear manner from one longitudinal end of the cover 24 to the other longitudinal end as shown in FIG. 5.

The cover 24 is flexibly coupled to the base 22 by way of a flexible coupling or hinge 40. The coupling 40 desirably comprises a flexible band 42 that can take any number of forms to mechanically connect the cover 24 to the base 22 while permitting pivotal movement of the cover 24 relative to the base 22 so as to enable engagement or disengagement of these parts, as described below. In the illustrated embodiment, the band 42 is formed of flexible material, desirably of the same material from which the base 22 and cover 24 are comprised. Advantageously, the hinge 40 is integrally molded with the base 22 and the cover 24 to form a unitary member, as noted above. The hinge 40 is located at an outer edge of the base 22 and the cover 24; however, the hinge 40 need not be laterally located at an extreme end of the base 22 or cover 24.

As best understood from FIG. 5, the width of the hinge 40, as measured in the longitudinal direction, is desirably less than that of either the base 22 or the cover 24 to allow some leeway or play when engaging or disengaging the cover 24 to the base 22. That is, this shape allows the hinge 40 to twist to some degree to compensate for some manufacturing tolerances; however, the hinge 40 can have at least as large of a longitudinal dimension as the base 22 and the cover 24.

The hinge 40 is desirably integrally formed along a common corresponding exterior surface of the cover 24 and base 22. In the illustrated embodiment the hinge 40 generally has a U-shape when the cover 24 is closed, and extends from both the base 22 and the cover 24 in the lateral direction to the side of the retainer 20. A gap, corresponding to a transverse height of the hinge, exists between the base 22 and cover 24. This gap, however, can be reduced or eliminated from the retainer for some applications by using a different hinge design.

Figure 8:
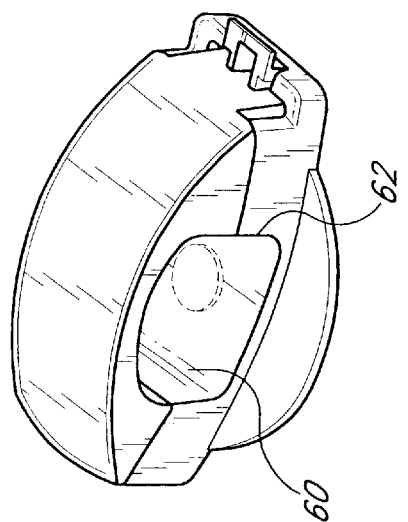
FIG. 8 illustrates a perspective view of the retainer of FIG. 4 with the cover in the closed position.

The hinge 40 enables the cover 24 to move between the open position and the closed positions. The open position, as illustrated in FIG. 4, is characterized by exposing the grooves 30, 36 in the base 22 and the cover 24 in the transverse direction and thereby spacing apart the base 22 and the cover 24. When in the open position, the retainer 20 is capable of receiving a portion (e.g., the Y-site 112) of the dialysis catheter 8. The closed position, as illustrated in FIG. 8, is characterized by the cover 24 lying in contact or near contact with the base 22 so as to position the upper groove 36 above the lower groove 30. When in the closed position, the retainer 20 surrounds the received portion of the catheter.

Figure 9:
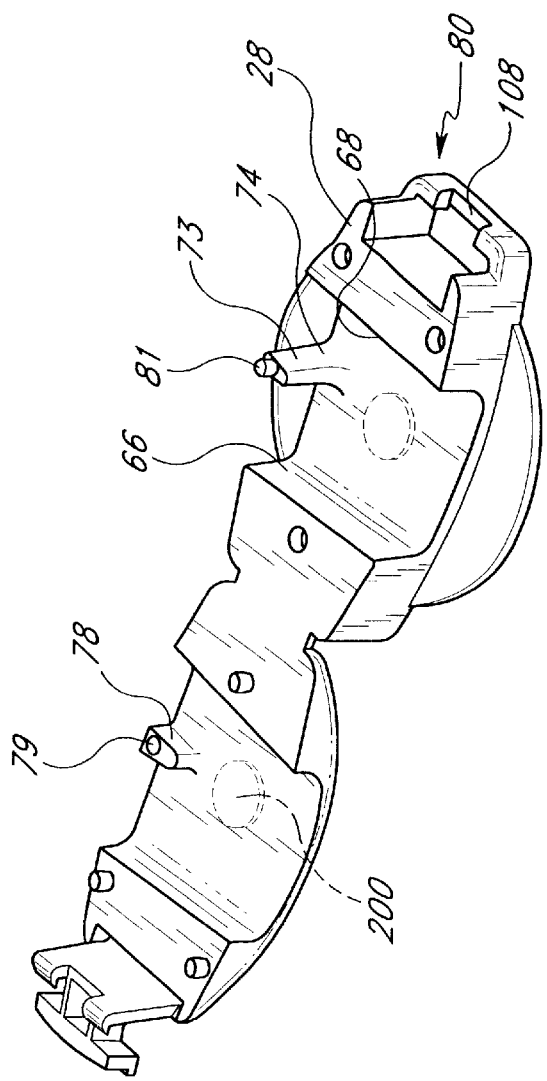
FIG. 9 illustrates a perspective view of the retainer of FIG. 8 with the cover in the open position.

The hinge 40 need not provide 180° of movement of the cover 24 relative to the base 22 to establish the closed position and a fully open position, as illustrated by FIGS. 8 and 9. For instance, the hinge 40 can permit a smaller degree of movement (e.g., 90°) between the base 22 and the cover 24 while still providing enough space to transversely insert the catheter into the retainer 20.

The grooves 30, 36 formed in the base 22 and the cover 24 define a channel 60 when the retainer 20 is closed. The channel 60 is capable of receiving a portion or length of the catheter and is generally configured to house, grip and secure the affected catheter portion. The channel 60 can have a variety of configurations, as discussed above in connection with the grooves 30, 36, in order to accommodate a particular medical article. In the illustrated embodiment, the channel 60 generally has circular cross-sectional shape at its proximal end 62 and a generally oblong cross-sectional shape at its distal end 64 (although, in the illustrated embodiment, the distal end 64 is divided by a pair of cooperating post, which will be described below). The channel smoothly tapers in cross-sectional size from its smaller proximal end 62 to its larger distal end 64. The channel 60 consequently generally has a truncated V-shape, as best understood by inspecting the shapes of the grooves 30, 36 in FIG. 5.

In the embodiment illustrated, the sides of the channel 60 are generally straight and diverge from each other. The walls of the channel 60 (and, thus, the grooves of the cover and base), however, need not be straight. This channel shape furthers retention of the catheter within the channel 60 to inhibit catheter movement through the channel, as discussed below.

Although the channel 60 can take the form of various shapes depending upon its application (i.e., depending upon a shape of the retained portion of the medical article for which the retainer is designed to be used), the channel 60 does have a sufficient length in the longitudinal direction to stabilize the catheter, rather than act as a fulcrum for the catheter, as mentioned above. That is, the retainer receives a sufficient length of the catheter to inhibit movement of the catheter in the lateral, longitudinal and transverse direction (i.e., to inhibit yaw, pitch and axial movement of the catheter), without kinking the catheter. Also, the wide-mouth shape (i.e., the large oval-shape) of the channel proximal opening eliminates an edge or surface over which the catheter could kink.

Figure 15:
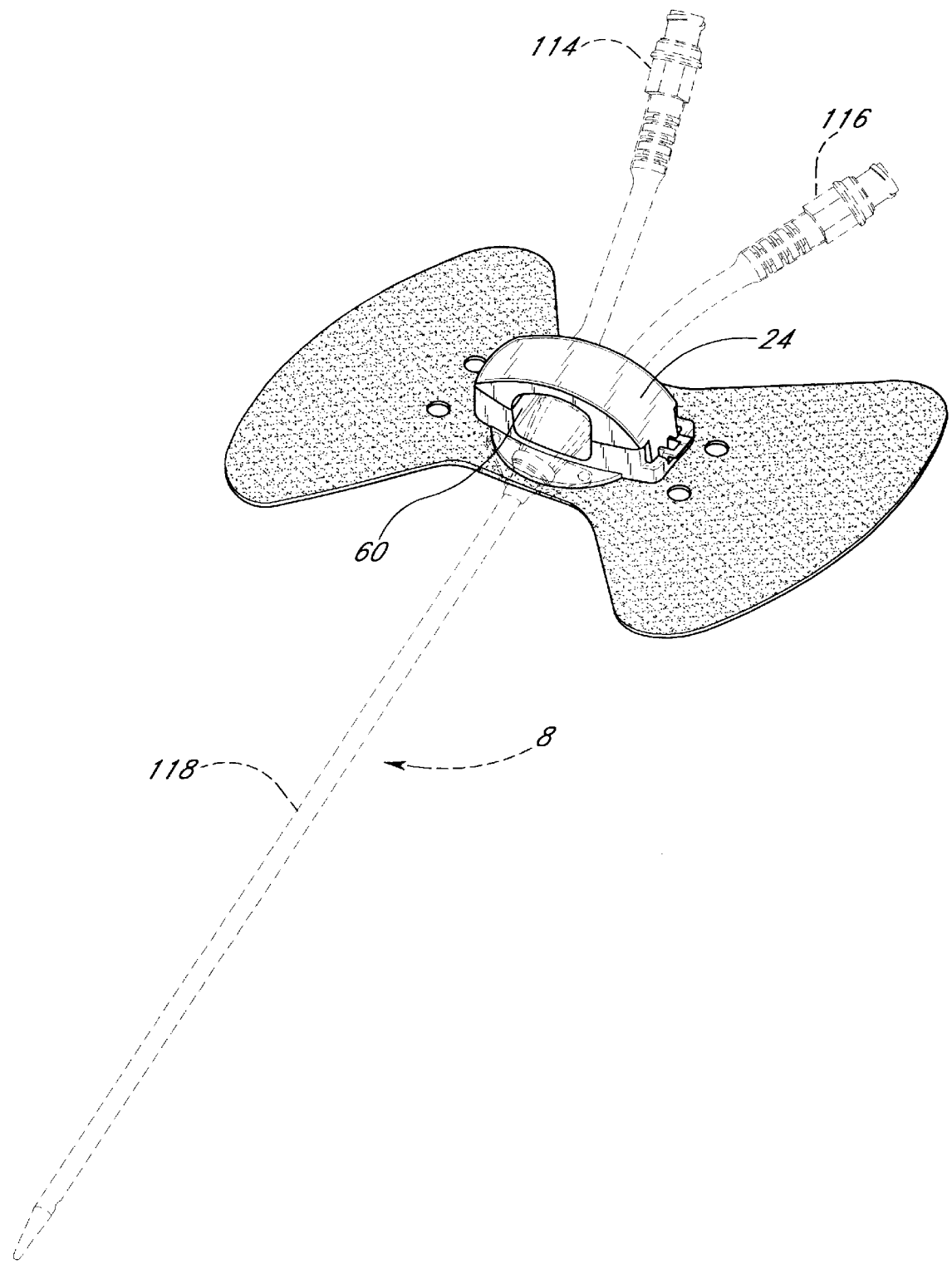
FIG. 15 illustrates a perspective view of the retainer of FIG. 14 with the cover in the closed position.

When the cover 24 is closed, a section of the catheter 8 is captured within the retainer 20 (as shown in FIG. 15). Thus, the retainer 20 at least restricts, if not prevents, lateral and transverse movement of the retained section of the catheter 8.

Additionally, as shown in FIG. 9, an adhesive spot 200 may also be advantageously disposed upon the inside of the cover within the upper groove. This adhesive spot may take the form of a glue dot. Such glue dots are desirably formed of a material which exhibits high resistance to shear and which can be peeled off of the catheter Y-site without leaving a residue. Such an adhesive is sold by All-Pak Inc. of New Berlin, Wis. as part number GD-06 "Super High Tack Glue Dot." Multiple glue dots may be used, or a single glue dot may be disposed on only one side of the channel of the retainer.

The adhesive spot 200 is represented in all figures as a glue dot shown in hidden lines on both the surface of the cover groove 36 and the base groove 30 (see FIG. 4). It is not necessary for multiple glue dots to be used; a single glue dot disposed upon either the cover groove or base groove may advantageously be used to provide greater frictional and transverse forces between the retainer 20 and the catheter.

Furthermore, the adhesive spot 200 need not be a single point of adhesive. In further preferred designs the adhesive spot may be a region composed of an elastic and compressively deformable material such Kraton® polymer compounds. Such a compound includes Dynaflex® G2706 available from GLS Corporation, as well as other thermoplastic elastomers or silicone or urethane epoxies.

This region also need not be round. In further preferred designs, a large region of the surface of the channel 60 may be covered with a suitable material, such as Kraton®. For instance, the entire surface of the lower groove 30 might be covered with a thin layer of adhesive to advantageously provide additional traction and transverse bias between the catheter and retainer.

Other means of producing an appropriate adhesive spot for use with various preferred embodiments of the present invention include without limitation: treating a portion of the surface of the channel chemically or electrically to adjust its surface friction or compressibility; spraying or spreading an adhesive coating onto a portion of the grooves of the retainer; attaching peel-off adhesive members to portions of the channel; injection molding regions of adhesive or compressible material, such as Kraton®, to a portion of the surface of the channel; or such other means as are known in the art.

Figure 7:
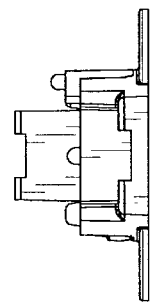
FIG. 7 illustrates a right side view of the retainer of FIG. 4.

Inhibiting movement of the catheter 8 in the longitudinal direction when the catheter 8 is secured within the channel 60 is also desirably accomplished by one or more retention mechanisms that associate with the channel 60. With reference to FIGS. 5, 6 and 7, one such retention mechanism involves the shape of the channel 60 itself. The interaction between the truncated V-shape of the channel 60 and a corresponding shape of the catheter Y-site 112 inhibits proximal longitudinal movement.

Figure 14:
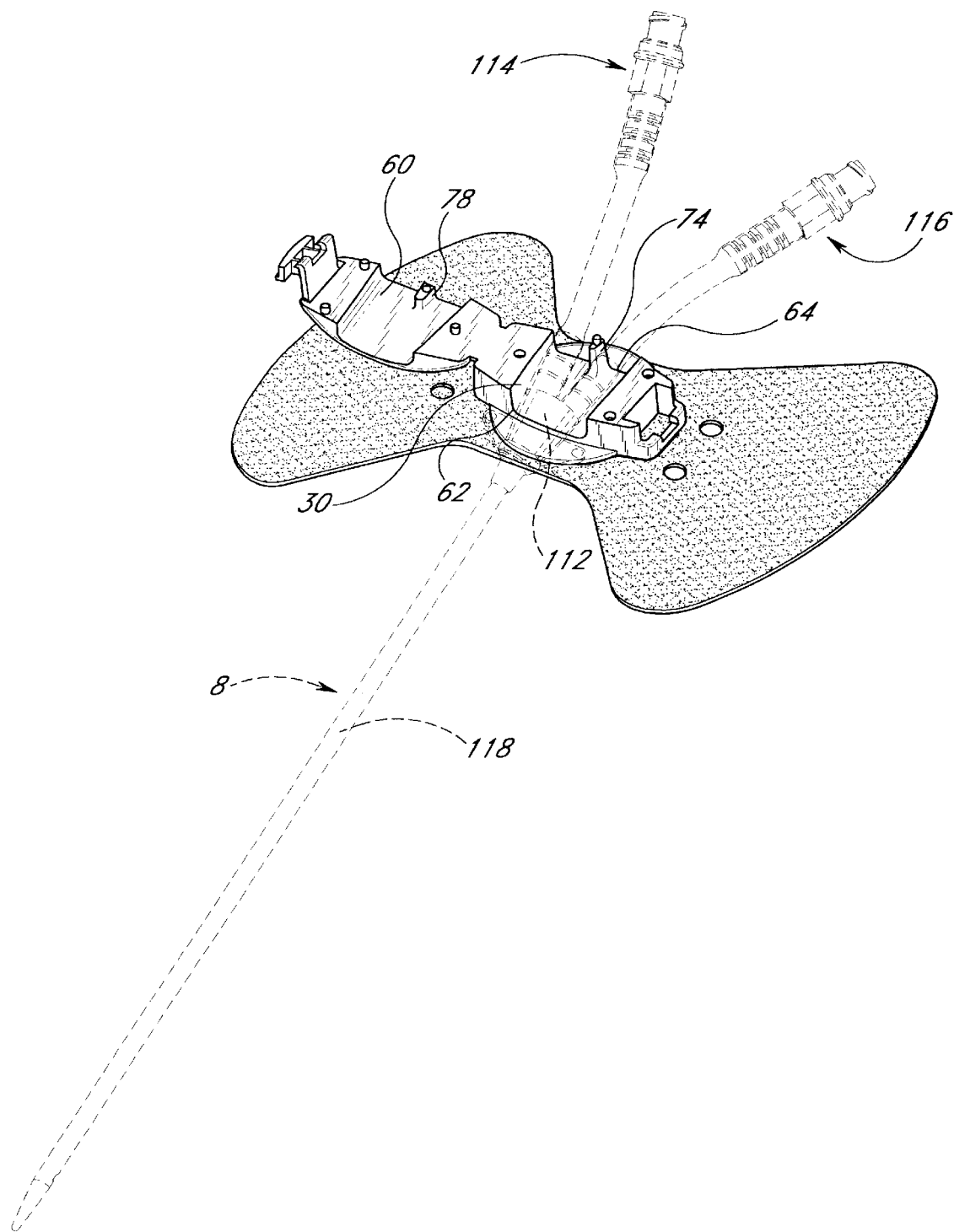
FIG. 14 illustrates a perspective view of the retainer of FIG. 4 with an exemplary dialysis catheter shown in position upon the retainer.

As best understood from FIG. 14, the proximal end 62 of the channel 60 is sized to receive only the main body 118 of the catheter 8. The distal end 64 of the channel 60 is sized to receive both branches 114, 116 of the catheter at the distal side of the Y-site 112. And between its distal and proximal ends 64, 62, the channel 60 is configured to receive the catheter Y-site 112.

In the illustrated embodiment, each side of the channel 60 is angled so as to provide a narrower channel on the proximal end than on the distal end. This is accomplished by angling the sides 66, 68 of the channel so that they converge toward the proximal end of the retainer. While the illustrated embodiment uses the same angle for each side of the channel, it may be advantageous for some applications to create the channel with different angles for the first side and second side of the channel.

The sides 66, 68 of the channel 60 desirably vary in a tapering or linear manner (although they may include a convex section as noted above). An angle of divergence between the first and second sides 66, 68 of the channel 60 is desirably between about 10° and about 70°, and more preferably is between about 30° and about 45°, and generally matches the angle at which the two branches 114, 116 of the catheter intersect, as seen in FIG. 14.

Because the catheter Y-site 112 is larger in cross-section than its main body 118, the Y-site 112 usually cannot be pulled proximally through the smaller proximal end 62 of the retainer channel 60. The shape of the channel 60 thus inhibits longitudinal movement of the catheter in the proximal direction.

Variations on the channel's shape of course are also possible, as noted above. For instance, the second side 68 of the channel 60 can vary from the first side 66 in a curvilinear manner and/or can include a gouge, protrusion or similar geometric abnormality so as to cooperate with or impinge upon a corresponding portion of the received catheter length. Also, there is no requirement that the sides of the channel be symmetrical to one another. Either the first 66 or second 68 side, or both sides, can vary in distance relative to the axis of the received catheter length so as to inhibit longitudinal movement of the retained section of the catheter 8. The channel, however, can have a straight or uniform cross-sectional shape where the retainer includes at least another mode of the retention mechanism.

The interaction between the surface of the retainer channel 60 and the catheter Y-site 112 also creates friction to inhibit longitudinal movement through the channel 60. The degree of interference between the catheter 8 and the retainer 20, however, cannot be so great as to significantly occlude the catheter 8.

The adhesive spot 200 forms an additional retention mechanism. When the cover is moved into the closed position, the glue dot or other adhesive spot will be captured between the inner surface of the cover and the upper surface of the Y-site of the dialysis catheter or other medical article. Once pressed between the cover and the catheter, the adhesive spot will tend to inhibit any shear motion between the two surfaces which it contacts. In this way, the adhesive resists both longitudinal and lateral motion of the catheter within the retainer.

As shown in FIG. 9, a retaining structure 73, which protrudes into the channel 60, can also be used to inhibit axial movement of the catheter. The retaining structure 73 forms an upstanding member transversely positioned relative to the anchor pad 12. The retaining structure 73 is arranged to lie between the branches at the catheter Y-site 112 retained by the retainer 20 so as to inhibit axial movement of the catheter 60 in the distal direction. Thus, in the illustrated embodiment, the combination of the tapering channel shape and the retaining structure 73 inhibits axial movement of the retained section of the catheter 8 in both the proximal and distal directions.

The retaining structure 73 desirably has a sufficient height to inhibit axial movement of the catheter 8 in the distal direction. For this purpose, the retaining structure 73 has a height, in the transverse direction, of at least about 25% of the height of the channel 60 at the location at which the structure is positioned. In the present application, the retaining structure desirably extends across channel 60.

In the illustrated embodiment, the retaining structure 73 is formed by a base post 74 and a cover post 78. The base post 74 desirably is integrally formed with the base 22, and is located in the channel 60 toward the distal end 64 of the channel 60. The cover post 78 is integrally formed with the cover 24 also at the distal end 64 of the channel 60. Although in the illustrated embodiment, the base post 74 and cover post 78 lie within the channel 60, the posts 74, 78 can be located outside the distal end 64 of the channel 60.

In one mode, the base post 74 is sized to extend to a position where its upper end lies near or contacts the webbing of the catheter 8 (see FIG. 14) that extends between the Y-site branches 114, 116. In the illustrated embodiment, the upper end of the post 74 lies generally even with the upper surface of the first and second sides 26, 28 of the base 20, as best seen in FIG. 6. The cover post 78 similarly extends to a point which is generally flush with a plane defined by the inner surfaces of the cover first and second sides 32, 34 that lie adjacent to the base 22.

As best seen in FIG. 6, the lateral position of the post 74 within the channel 60 corresponds with the merge point between the inflation lumen branch 114 and the discharge lumen branch 116 of the Dialysis catheter 8. The post 74 divides the channel 60 at the channel's distal end 64.

The cover post 78 is configured and arranged on the cover 24 in a manner similar to that described above in connection with the post 74 on the base 22. In the illustrated embodiment, the post 78 thus generally opposes the base post 74. By this particular design, as understood from FIG. 5, the combination of the posts 74, 78 and the channel 60 define a generally Y-shaped recess between the channel's proximal and distal ends 62, 64.

Figure 11:
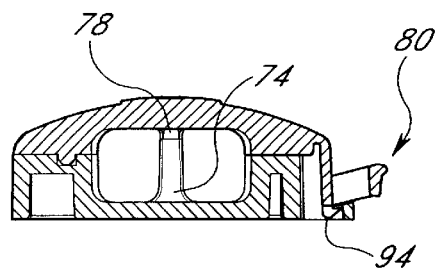
FIG. 11 illustrates a cross sectional view of the retainer of FIG. 10 with the cover in the closed position.
Figure 12:
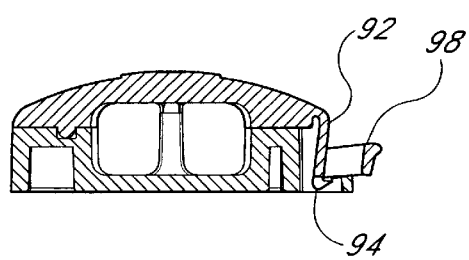
FIG. 12 illustrates a cross sectional view of the retainer of FIG. 10 with the latch released and the cover in the closed position.
Figure 13:
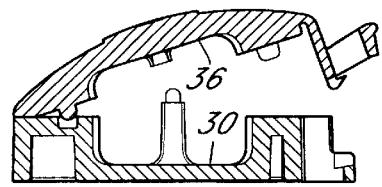
FIG. 13 illustrates a cross sectional view of the retainer of FIG. 10 with the cover unlatched and slightly open.

In the illustrated embodiment, the transverse height of the cover post 78 is less than that of the base post 74. The posts 74, 78, however, can have equal heights or the cover post 78 can be longer than the base post 74. Together though, as best seen in FIG. 11, the posts 74, 78 desirably span the channel 60 in the transverse direction, except for a small gap formed at their interface. This gap can be slightly less than a thickness of the catheter webbing between the Y-site branches 114, 116, for the reasons described below, and corresponds to the gap provided by the hinge 40 when the cover 24 is closed.

The posts 74, 78 thus extend between these two branches 114, 116 of the catheter 8 when the catheter Y-site 112 is positioned within the channel 60. Together the posts 74, 78 can act as a stop against longitudinal movement of the catheter 8 in the distal direction. That is, longitudinal movement in the distal direction causes the catheter Y-site 112 to contact the posts 74, 78. The posts 74, 78, being of rigid construction, prevent further longitudinal movement.

Although the posts 74, 78 can have a variety of cross-sectional shapes, the posts 74, 78 desirably have a generally triangular cross-sectional shape in the present application so as to correspond to the space between the two catheter branches 114, 116 at the Y-site 112. The proximal edge of the posts, however, advantageously is rounded to eliminate sharp contact between the catheter 8 and the retainer 20 at this location.

The posts 74, 78 can also include interengaging elements to interlock the posts 74, 78 in the transverse direction and prevent the catheter 8 from being pulled through the gap between their ends. In the illustrated embodiment, a pin or projection 81 and a corresponding receptacle 79 are arranged between the interfacing ends of the posts 74, 78. As best seen in FIG. 9, the receptacle 79 is formed at the transverse end of the base post 74, extending into the post 74 in a transverse direction from an interface surface of the post 74. The projection 81 extends from an end of the cover post 78 in a direction parallel to a transverse axis of the post 78. The projection 81 is configured to fit within the receptacle 79. When the cover 24 is closed, the pin 81 extends into the receptacle 79 to interlock together the posts 74, 78.

Another possible retention mechanism to inhibit axial movement of the catheter 8 relative to the retainer 20 involves protuberances that are arranged to cooperate with one another when the cover 24 is closed. For instance, in one mode, the cooperating posts 74, 78 can be arranged to capture a structural portion of the catheter (e.g., the catheter webbing) between them without substantially occluding an inner lumen of the catheter 8. In another mode, the projection 81 can be employed without the receptacle 79 to simply pin a portion of the catheter (e.g., its webbing) against a surface of the retainer 20. For instance, the projection 81 can extend from a portion of either the base 22 or the cover 24 and cooperate with a corresponding surface (be it a post, platform or channel surface) that opposes the projection 81 when the cover is closed. The projection 81 would protrude into the portion of the catheter and pin it against the corresponding surface.

Alternatively, the projection 81 can be used with the receptacle 79 to capture a section of the catheter. When the cover 24 is closed, the projection 81 could force a portion of the catheter body 8 into the receptacle 79 to capture a structural portion of the catheter 8 between these components without occluding an inner lumen of the catheter. This engagement of the retainer 20 with the catheter body 8 would inhibit axial catheter movement relative to the retainer 20.

Latch

To firmly hold the affected catheter portion within the channel, the base 22 and the cover 24 include interengaging structure to couple them together in the closed position. In the illustrated embodiment, as best seen in FIGS. 10 to 13, a latch mechanism 80 is used to secure the cover 24 to the base 22. The latch mechanism 80 comprises at least one moveable keeper 88 and at least one latch 90. The keeper 88 is arranged on the cover 24 while the latch 90 is arranged on the base 22; however, these components can be flip-flopped on the base and the cover.

Figure 10:
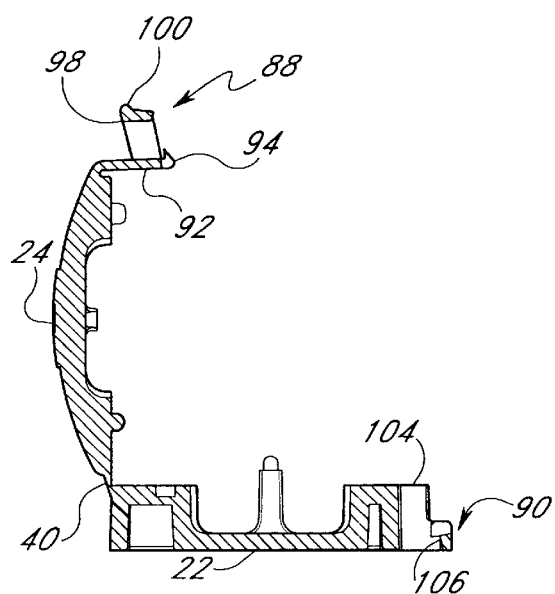
FIG. 10 illustrates a cross sectional view of the retainer taken along line 10—10 of FIG. 5 with the cover in the open position.

As best seen in FIG. 10, each keeper 88 includes a bar 92 extending toward the base 22 from the second side 34 of the cover 24. Two tangs 94 are formed at a lower end 96 of the bar 92. Desirably, the lower end 96 of the tangs 94 are relatively blunt and smooth to prevent them from puncturing the gloves or skin of a healthcare provider or catching on other materials. An operator lever 98 extends to the side of the bar 92 and includes an enlarged platform or ear 100 at its outer end. The operator lever is angled upwardly from the bar when the cover is in the closed position. In this way, downward force upon the operator lever produces a component which causes the bar to deflect inwardly, allowing the tang to disengage from the latch. The entire keeper 88 desirably is formed with the cover 24 to form a unitary piece.

The latch 90 includes a receptacle 104 that receives the bar 92 and the tangs 94. The latch receptacle 104 includes inner notches 106 into which the tangs 94 snap when the cover 24 is in the closed position; however, the tangs can be arranged in the receptacle and the notches be positioned on the bar to accomplish the same effect. The latch 90 desirably is formed with the base 22 as a unitary piece.

In the illustrated embodiment there are two tangs 94 and two notches 106 disposed symmetrically from front to back on the retainer. Each notch 106 is arranged to receive one of the keeper tangs 94 when the cover 24 is closed.

An entrance of the receptacle 104 includes chamber edges. The chamfer edges slope inward toward the center of the receptacle 104 to cause the keeper bars 92 to bend inward when inserting the keepers 88 into the latch receptacle 104.

As best understood from FIGS. 9 and 10, the second side 28 of the base 22 also includes a slot 108 to receive a portion of the operator levers 98 and the bar 92 of the keepers 88 when the associated tangs 94 are inserted into the receptacle 104.

In operation, the cover 24 can swing toward the closed position. The relatively thin strip of material forming the coupling allows the hinge 40 to bend when finger pressure is exerted on the cover 24 to close it. The lower ends of the tangs 94 contact the chamfered edges 107 of the latch receptacle 104 when the cover 24 nears its closed position. Continued pressure forces the bar 92 inward toward the channel to permit the tangs 94 to pass through the receptacle. The slot 108 of the receptacle 104 receives the operator lever 98 as the tangs 94 are pushed further into the receptacle 104. The tangs 94 snap into the notches 106, under the spring force provided by the deflected bar 92 when the cover 22 sits atop the base 24. The interaction between the tangs 94 and the corresponding surfaces of the notches 106 hold the cover 24 in this position. As best seen in FIG. 11, the operator lever 98 extends to the lateral side of the base 24 when the cover 24 is latched.

A medical attendant presses downward on the operator lever to open the latch mechanism 80. A downwardly force applied to the angled outer surface exerts an inward force component which deflects the bar 92 inward and releases the tangs 94 from the notches 106. The inherent spring force stored in the bent hinge band assists with providing a transverse force that moves the keeper 88 out of the receptacle 104. The medical attendant can then open the cover 24 and expose the inner grooves 30, 36 of the base 22 and the cover 24.

The releasable engagement between the cover 24 and the base 22 allows the same retainer 20 to be used even when opened and closed multiple times. This allows for repeated attachment and reattachment of the catheter to the anchoring system 10. In addition, the hinged connection connecting the cover 24 to the base 22 ensures that the cover 24 will not be lost or misplaced when the catheter is detached from the anchoring system 10. The medical attendant wastes no time in searching for a cover, nor in orienting the cover prior to latching.

Variations

Additional securement of the medical article may be provided using further techniques to those described above. These can include the use of friction ridges and securement barbs within the channel of the retainer as will be described below.

Friction ridges may be located on the channel surface as a further retention mechanism to inhibit axial movement of the catheter. These ridges are integrally formed with the base and the cover and project into the channel. Such ridges may be used in addition to the retention mechanisms described above, as well as either with or without the securement barbs described below.

The ridges are desirably of smooth solid construction; however, they can be of hollow construction. The ridges in the illustrated embodiment have generally triangular cross-sectional shapes and angle toward one end of the channel (e.g., the distal end). The ridges, however, can have other cross-sectional shapes which would interfere with axial movement of the catheter through the channel.

Each of the ridges desirably has a front wall or leading edge that forms an angle of less than degrees as measured between the front wall and the channel surface. The ridges slightly protrude into the channel, desirably at a transverse distance of between 0.1 to 10 mm for the given application. The ridges also lie generally normal to a longitudinal axis through the channel.

When so arranged, the friction ridges gently, but securely bite or press into an outer surface of the catheter Y-site. Such contact does not occlude or otherwise meaningfully impair fluid flow in the catheter lumens because of the compliant nature of the catheter body material and because of the degree to which the ridges bite into the catheter body. This degree of contact, however, coupled with the angular orientation of the ridges inhibits movement of the catheter, especially in a direction opposite of that in which the ridges are angled.

One or more securement barbs can also be used to retain the catheter in the longitudinal direction. Each barb has a generally conical shape with a blunt tip. The barb in the present application desirably extends into the channel by an amount ranging between about 0.1 mm and about 3 mm.

The retainer may advantageously include at least one set of securement barbs, indicated collectively by reference numeral, the barbs being arranged within the channel to cooperate with one another. The barbs advantageously are arranged within the same general lateral plane (i.e., a plane defined by the lateral and transverse axes), and are spaced apart from one another. In addition, the barbs desirably are spaced on generally opposite surfaces of the channel in a staggered arrangement. That is, the position of the barbs alternate between the cover surface and the base surface in the lateral direction. The resulting overlapping pattern of the barbs securely holds the catheter without imparting torque to the catheter if pulled in a longitudinal direction. In the illustrated embodiment, one barb is positioned on the cover surface and is generally equally distanced in the lateral direction from the adjacent side of the channel and the adjacent side of the post. A pair of barbs is positioned on the base surface. These barbs are spaced apart from one another and the pair is symmetrically positioned relative to a transverse axis that extends through the barb on the cover surface.

The retainer may also further comprise a second set of barbs in an additional preferred embodiment. These are arranged generally in accordance with the above description; however, fewer number of barbs, as well as fewer sets, can also be used. In one particular embodiment, one set of barbs is placed between the posts 74, 78 and the first sides 26, 32 of the cover 24 and the base 22, and the other set of barbs is placed between the posts 74, 78 and the second sides 28, 34 of the cover 24 and the base 22. The barbs of the first set are desirably angled toward the distal end 64 of the channel 60 to inhibit movement of the catheter's inflation lumen branch 114 in the proximal direction when the catheter 8 is pulled proximally, as well as when the catheter 8 discharge branch 116 is pulled distally. The barbs of the second set, however, are desirably angled toward the proximal end 62 of the channel 60 to inhibit movement of the catheter 8 when the catheter is pulled distally.

The anchoring system described herein is especially adapted to arrest axial movement of a catheter with a slippery coating, as well as to hold the catheter against the patient. For this purpose, the anchoring system utilizes one or more retention mechanisms. The anchoring system accomplishes this without meaningfully impairing (i.e., substantially occluding) the fluid flow through the catheter to a degree that would create complications. As described, such retention mechanisms involve, among others, the shape of the channel that retains a section of the catheter, retaining structure either aligned with or positioned within the channel, one or more securement barbs or friction ridges that bite into the catheter body without substantially occluding the catheter drainage lumen, and cooperating members that come together to clamp onto or pin down a portion of the catheter (e.g., a webbing formed between the branches at the Dialysis catheter Y-site).

Operation

Figure 16:
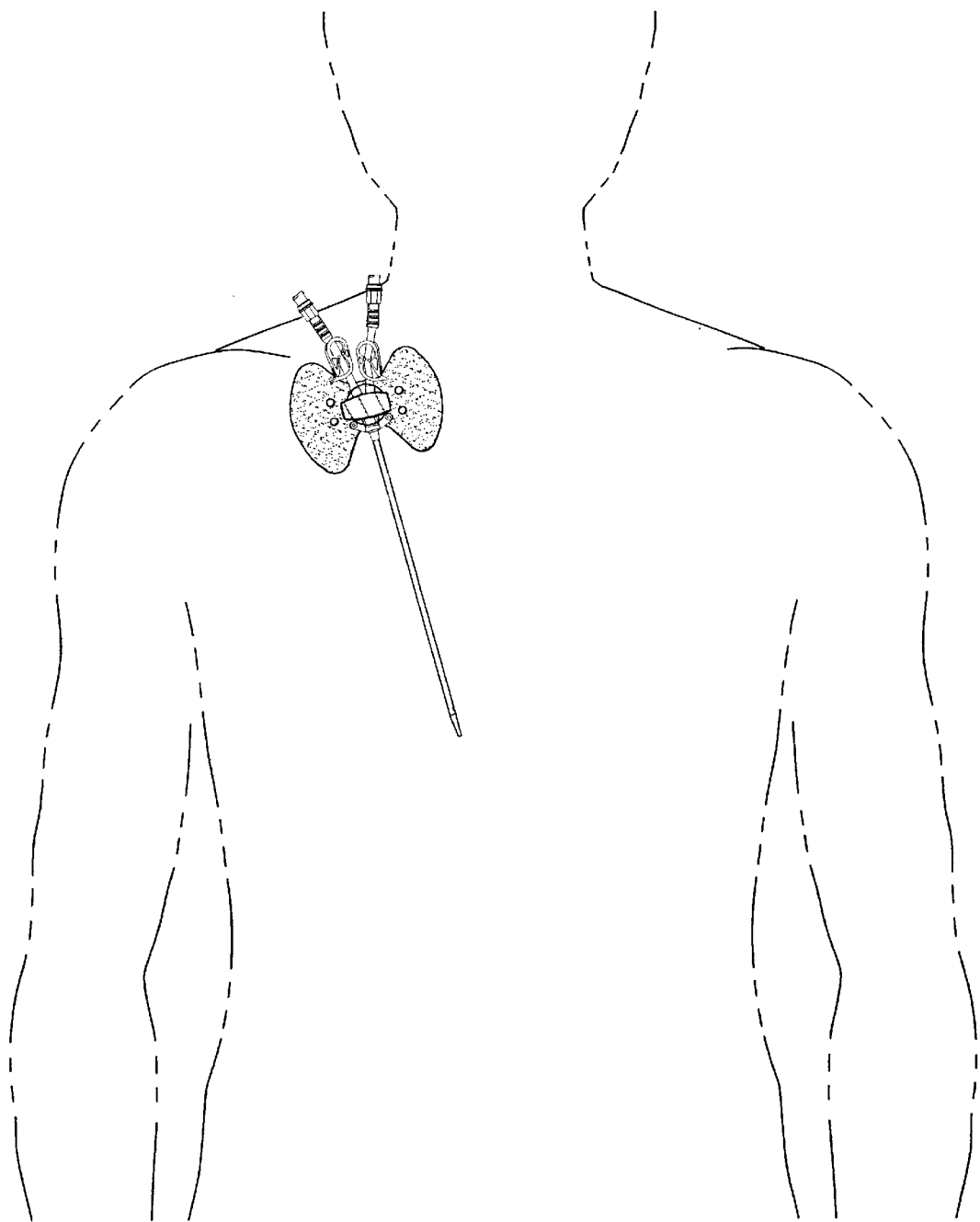
FIG. 16 illustrates a perspective view of the anchoring system of FIG. 1 in use upon a patient.

As illustrated in FIGS. 14 to 16, a medical attendant can secure a dialysis catheter (or other medical article) to a patient using the above-described anchoring system (or a readily apparent modification thereof). The medical attendant first opens the retainer 20 to expose the groove 30 on the base 22. Once opened, a catheter 8 can be transversely aligned over the groove 30. The catheter 8 can then be placed into the channel 60. If the channel 60 is formed with a post 74 (or another protuberance) for use with a Y-site, the first and second branches 114, 116 are aligned around the post 74 and the catheter Y-site 112 is aligned to securely fit within the remaining groove confines. Once the catheter 8 is so aligned and placed into the groove 30, the cover 24 is closed and latched, in the manner described above. The shapes of the grooves 30, 36 ensure that the channel supports the catheter Y-site 112 on at least diametrically opposed sides thereof along the entire retained length of the catheter Y-site, and places a portion of the catheter Y-site in contact with the adhesive spot 200. This not only enhances frictional contact between the retainer 20 and the catheter 8, but it also prevents the catheter 8 from kinking or crimping with the retainer 20 and thereby occluding one or more of the catheter lumens.

In the illustrated embodiment, the posts 74, 78 come together with the projection 81 inserting into the receptacle 79 when the cover is closed. The posts 74, 78 therefore are interlocked in this position to form a stop on the distal side of the Y-site 112 that spans entirely across the channel's transverse length. Any securement barbs (if present) also bite into the body of the catheter Y-site 112 to resist movement of the catheter branches 114, 116 in a direction opposite of the direction in which they are angled.

Because most dialysis catheters are approximately the same transverse height, a single size retainer with a single sized channel can be used to secure most catheters. The material of the retainer is slightly flexible, which helps the retainer accommodate catheters which may include plastic hubs of larger thickness located at the Y-site. Furthermore, the adhesive spot 200 disposed upon the channel is desirably compressible in the transverse direction such that a larger catheter will simply compress the adhesive spot further without changing the operation of the retainer in any substantial manner.

If the catheter 8 is pulled in the proximal direction, the tapered shape of the channel 60 prevents the larger distal end of the Y-site 112 from pulling through the retainer. And if the retainer employs posts or projections that clamp onto or pin the catheter webbing within the channel, then this engagement between the retainer and the catheter would further secure the catheter in place. If the catheter is pulled in the distal direction, the interlocked posts 74, 78 and action of the adhesive spot inhibit this movement.

The retainer 20 thus inhibits longitudinal movement of the catheter 8 relative to the retainer, even when used with a lubricated catheter. The holding effect provided by each of the retention mechanisms, however, does not substantially occlude the lumens of the catheter. The interaction of the protuberances (i.e., the posts and/or projection) only affects the catheter webbing (or like structure) and does not bear against the catheter body. Likewise, the interaction between the shape of the channel and posts restricts movement of the catheter in both axial directions, but does not crimp or kink the catheter body when it is inserted within the channel and about the posts. And although the securement barbs bear against the catheter body, their limited bite does not significantly occlude or penetrate the corresponding catheter lumen.

Similarly, the action of the adhesive spot 200 in all cases acts along the surface of the Y-site of the catheter to inhibit longitudinal and lateral motion between the catheter and the retainer. Because this force is exerted at the Y-site and primarily in a direction parallel to the surface of the catheter, the retention force provided by the adhesive spot does not tend to occlude the lumen of the catheter.

Additionally, many dialysis catheters in use include a winged section, traditionally used for attachment to other types of anchoring devices. Additional securement may be provided to the catheter by placing the catheter into the channel of the retainer of the present invention such that the winged section lies proximal of the retainer but flush against it. In this way, when the cover of the retainer is closed and secured, the width of the winged portion of the catheter will prevent it from being pulled into the channel of the retainer. This provides a further inhibition to distal migration of the catheter upon the patient.

The various embodiments of the anchoring systems described above in accordance with the present invention thus provide a means to secure a dialysis catheter or other medical article to a patient releasably. The catheter may be released from the anchor and the dressing changed without dislodging the catheter. The anchoring system inhibits longitudinal, lateral, and transverse motion of the catheter upon the patient once secured within the retainer.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the shape of the groove may be designed to accommodate a catheter with a large Y-site by using an un-tapered channel while retaining the latch and keeper design of the illustrated embodiment. Or the adhesive spot could be removed from a particular design while still making use of the retaining post to pin a portion of the catheter Y-site in place. In addition to the variations described herein, other known equivalents for each feature can be mixed and matched by one of ordinary skill in this art to construct anchoring systems and retainers in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A catheterization system comprising:
   a catheter including a branching site at which point the elongated body of the catheter separates into two elongated bodies and also including a winged catheter portion disposed proximal of the branching site;
   an anchoring system comprising an anchor pad and a retainer,
   the anchor pad comprising an upper surface and a lower surface, at least a portion of the lower surface formed with an adhesive layer, and
   the retainer comprising a base, a cover and an adhesive spot, the base having a substantially disc shaped lower surface which is attached to the upper surface of the anchor pad, and the cover being pivotally coupled to the base and movable between an open position and a closed position, the cover and the base cooperating to define a channel when the cover lies in the closed position and being configured to receive at least a portion of the catheter including the branching site, and the adhesive spot being disposed upon the channel such that at least when the cover is in the closed position, the adhesive spot lies in contact with both the retainer and a portion of the catheter and inhibits motion of the catheter within the channel of the retainer, the retainer further comprising at least one retainer member projecting into the channel and arranged to engage a portion of the catheter to inhibit axial movement of the catheter through the channel, and the retainer further comprising a latching mechanism operable between the base and the cover to selectively secure the cover to the base when the cover is in the closed position.

2. A catheterization system as in claim 1 wherein the winged portion of the catheter is positioned proximal to the retainer such that when the cover is secured over the retained portion of the catheter the winged portion of the catheter is inhibited from moving distally into the channel.

3. An anchoring system for securing an elongated medical article to the skin of a patient, comprising:
   an anchor pad having an upper surface and a lower surface, at least a portion of the lower surface formed with an adhesive layer;
   a retainer attached to the upper surface of the anchor pad, and comprising a base, a cover and an adhesive spot, the base having a substantially disc shaped lower surface which is attached to the upper surface of the anchor pad, and the cover being pivotally coupled to the base and movable between an open position and a closed position, the cover and the base cooperating to define a channel when the cover lies in the closed position and being configured to receive at least a portion of the elongated medical article, and the adhesive spot being disposed upon the channel such that at least when the cover is in the closed position, the adhesive spot lies in contact with both the retainer and a portion of the medical article and inhibits motion of the medical article within the channel of the retainer;
   at least one retainer member projecting into the channel and arranged to engage a portion of the medical article to inhibit axial movement of the medical article through the channel; and a latching mechanism operable between the base and the cover to selectively secure the cover to the base when the cover is in the closed position.

4. An anchoring system as in claim 3 wherein the adhesive spot exerts a frictional force between the surface of the medical article and the surface of the channel which inhibits relative motion between the medical article and the retainer.

5. An anchoring system as in claim 3 wherein the adhesive spot exerts a transverse force between the surface of the channel and the medical article to bias the retained portion of the medical article against the channel of the retainer.

6. A retainer for securing an elongated medical article to an anchor pad disposed upon the skin of a patient, comprising:

a base;

a cover which is pivotally coupled to the base and movable between an open and a closed position; and a latching mechanism operable between the base and the cover to selectively secure the cover to the base when the cover is in the closed position, the latching mechanism including a keeper and a latch, the keeper having at least one member capable of interengaging with at least a portion of the base, and the latch having a recess which accepts at least a portion of the member when the cover is in the closed position, the keeper also including an operator lever that can be actuated by the fingertip of a medical attendant to deflect the member of the keeper inwardly to disengage the member from the recess of the latch in order to move the cover from the closed to the open position, the latch also including a relief within which the operator lever lies when the latch is in the closed position and which allows the member to deflect inward as the cover is moved from the open to the closed position.

7. A method of releaseably anchoring an elongated medical article including a branching site onto a patient which permits the medical article to be retained in the same position relative to the patient, comprising:

providing an anchoring device which provides an adhesive lower surface, and a retainer comprising a base, a cover, a compressible member and a retaining member, the base further comprising at least a groove, and the base and the cover together forming a channel when the cover is secured in position over at least a portion of the base;

inserting at least the branching site of the medical article into the groove such that at least one branch of the medical article lies to each side of the retaining member;

positioning the cover over at least a portion of the groove;

securing the cover in a position overlying the covered portion of the groove to press a retained portion of the medical article against the compressible member to provide adhesion between the compressible member and the retained portion of the medical article; and securing the anchoring device to the skin of the patient via the adhesive lower surface of the anchoring device.

8. A method of releaseably anchoring an elongated medical article including a branching site onto a patient which permits the medical article to be retained in the same position relative to the patient, comprising:

providing an anchoring device which provides an adhesive lower surface, and a retainer comprising a base, a cover, a compressible member and a retaining member, the base further comprising at least a groove, and the base and the cover together forming a channel when the cover is secured in position over at least a portion of the base;

inserting at least the branching site of the medical article into the groove such that at least one branch of the medical article lies to each side of the retaining member;

positioning the cover over at least a portion of the groove;

securing the cover in a position overlying the covered portion of the groove to press a retained portion of the medical article between the compressible member and a side of the channel; and securing the anchoring device to the skin of the patient via the adhesive lower surface of the anchoring device.

9. A method for anchoring an elongated medical article with a winged portion located proximally of a branching site onto a patient, which permits the position of the medical article to be maintained relative to the patient, comprising:

providing an anchoring device which provides an adhesive lower surface, and a retainer comprising a base and a cover;

inserting a section of the medical article into a groove of the base of the retainer such that the winged portion of the medical article is disposed proximal of the base and adjacent to the base; and positioning the cover over at least a portion of the groove and securing the cover in a position overlying the portion of the groove such that the winged portion of the medical article is inhibited from moving distally into the groove; and securing the anchoring device to the skin of the patient via the adhesive lower surface of the anchoring device.

* * * * *

UNITED STATES PATENT AND TRADEMARK OFFICE
CERTIFICATE OF CORRECTION

PATENT NO. : 6,413,240 B1
DATED : July 2, 2002
INVENTOR(S) : Bierman et al.

It is certified that error appears in the above-identified patent and that said Letters Patent is hereby corrected as shown below:

Column 7,
Line 64, please delete "baste" and insert -- base --.

Signed and Sealed this

Fifth Day of August, 2003

JAMES E. ROGAN
*Director of the United States Patent and Trademark Office*